United States Patent [19]

Crews

[11] Patent Number: 4,886,063

[45] Date of Patent: Dec. 12, 1989

[54] REUSABLE THERAPEUTIC DEVICE

[76] Inventor: Beverly J. Crews, 1019 Richard St., Miamisburg, Ohio 45342

[21] Appl. No.: 213,292

[22] Filed: Jun. 29, 1988

[51] Int. Cl.$^4$ .............................................. A61F 7/10
[52] U.S. Cl. ..................................... 128/403; 62/372; 62/530
[58] Field of Search ................. 62/371, 372, 529, 530; 128/402, 403

[56] References Cited

U.S. PATENT DOCUMENTS

| | | | |
|---|---|---|---|
| 2,595,328 | 5/1952 | Bowen | 128/403 X |
| 3,822,705 | 7/1974 | Pilotte | 128/403 X |
| 4,311,022 | 1/1982 | Hall | 62/372 X |
| 4,324,111 | 4/1982 | Edwards | 62/530 X |
| 4,344,303 | 8/1982 | Kelly, Jr. | 62/530 |
| 4,399,668 | 8/1983 | Williamson | 62/372 X |
| 4,575,097 | 3/1986 | Brannigan et al. | 62/530 X |
| 4,576,169 | 3/1986 | Williams | 128/403 X |
| 4,676,247 | 6/1987 | Van Cleve | 128/403 X |
| 4,753,241 | 6/1988 | Brannigan et al. | 62/530 X |

Primary Examiner—Lloyd L. King
Attorney, Agent, or Firm—Ralph L. Marzocco

[57] ABSTRACT

Therapeutical application of elevated or depressed temperatures to various afflicted portions of an animal or human body with a multilayered device combining protective and insulative means with heating and cooling means renders pain less acute, alleviates disease, reduces body temperature, stimulates circulatory and respiratory systems. The heating and cooling means features an array of non-communicating chambers enclosing packets containing a thermoresponsive mixture while the protective and insulative means features a layer of resilient material and a layer of fabric-backed covering material. The reusable therapeutic device of the present invention can be manufactured in various sizes and shapes to conform to the contours of any animal or human body area and if damaged, can be easily repaired or the damaged part can be easily replaced.

20 Claims, 2 Drawing Sheets

U.S. Patent    Dec. 12, 1989    Sheet 1 of 2    4,886,063
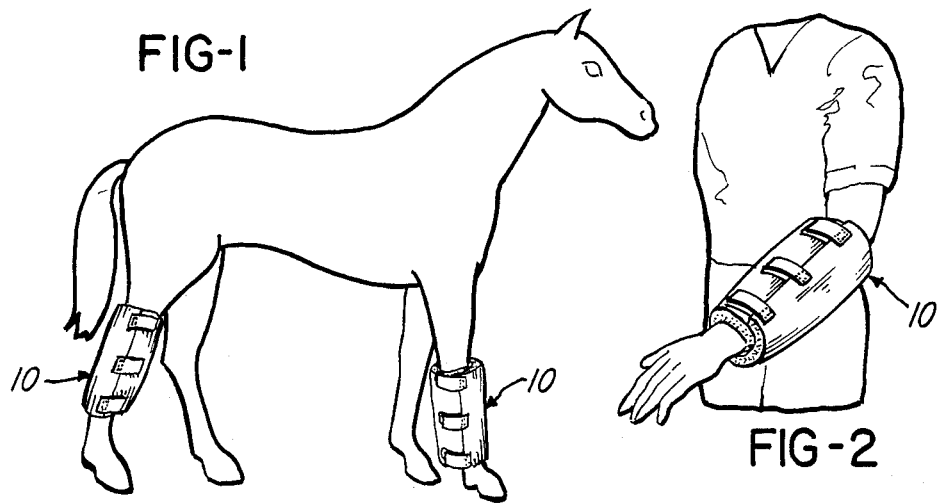
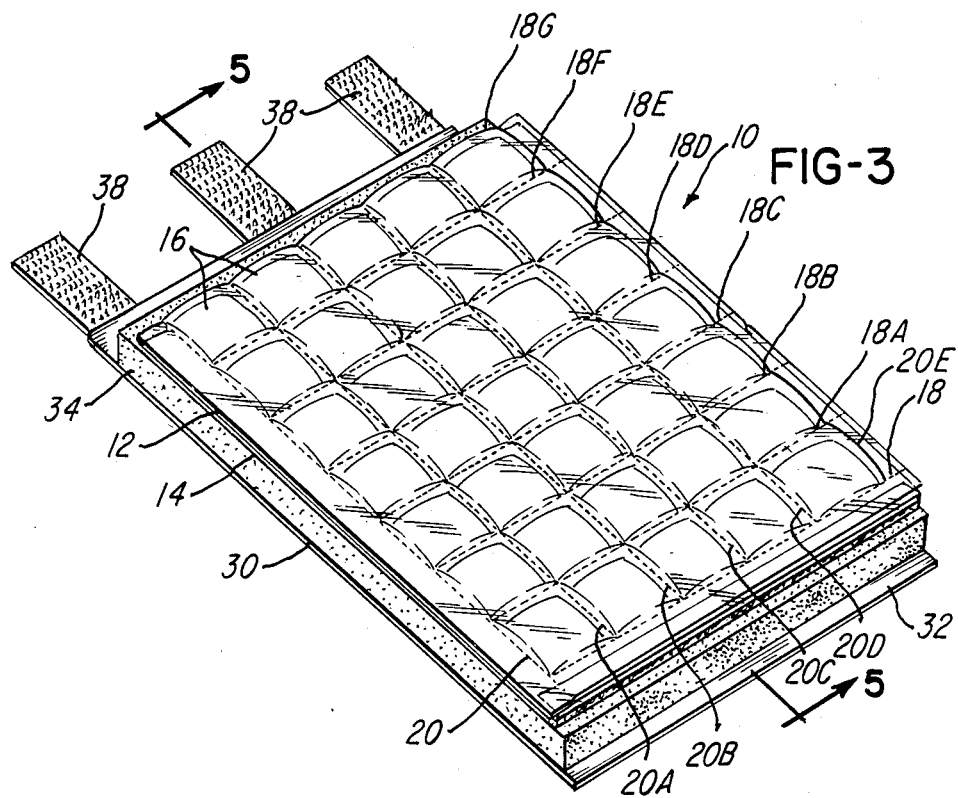

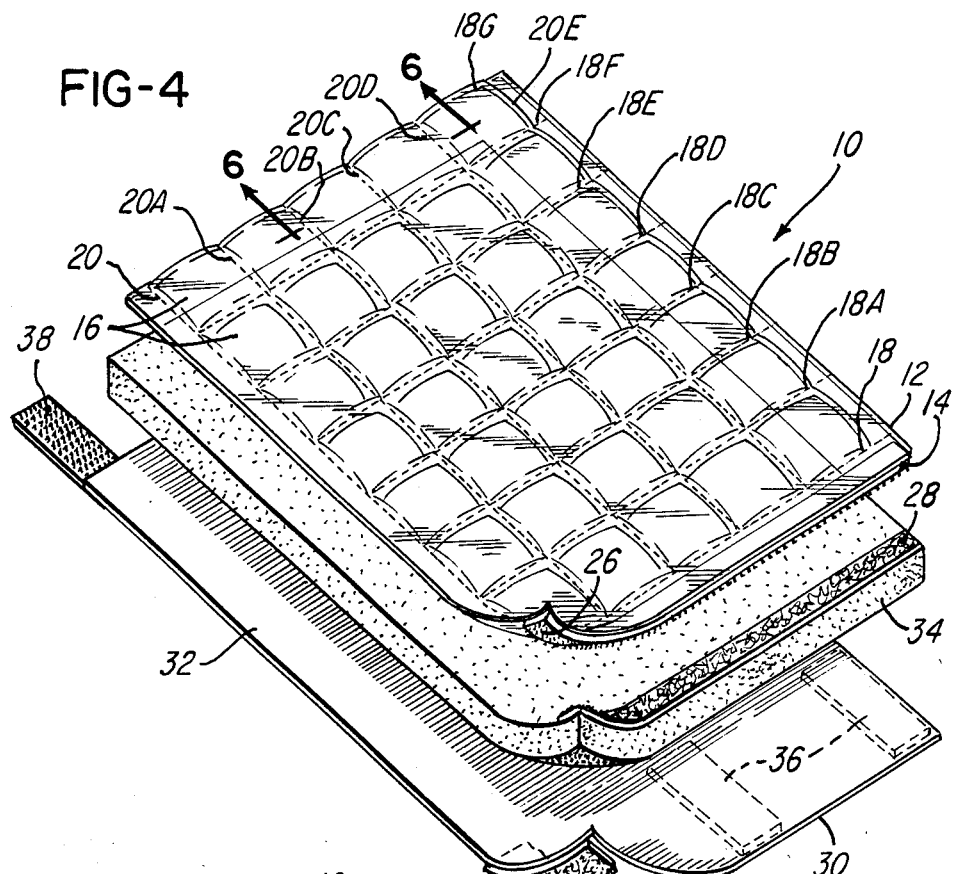
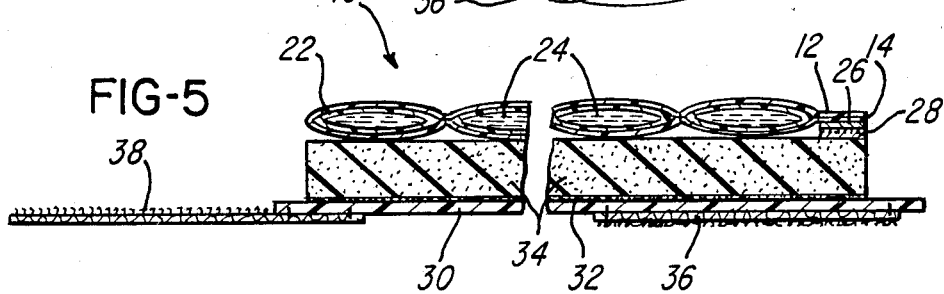
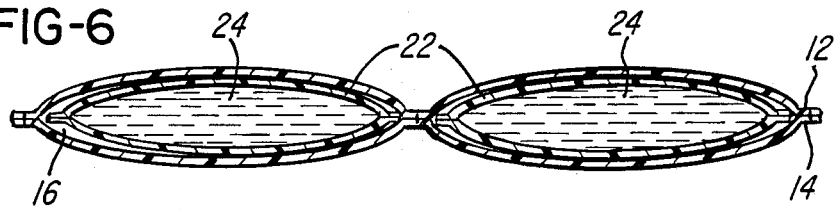

REUSABLE THERAPEUTIC DEVICE

BACKGROUND OF THE INVENTION

1. Field of the Invention

The present invention generally relates to a reusable therapeutic device. More particularly, the invention relates to a reusable therapeutic device which may be used for heating or cooling an animal or human body.

2. Description of the Prior Art

General or local therapeutic heating or cooling of an animal or human body is well known in the medical art. Heat has been directed to localized portions of such bodies to dull pain in the sensory nervous system by soothing the many terminals of nerves to the area affected, to alleviate disease by dilating the network of body vessels which lie below the skin and in the muscles so that more blood (including the very useful leucocytes which are the antagonists of germs) is brought to the surface, and to reduce the temperature of a body through the medium of the pores by getting rid of surplus sweat derived from the suffused capillaries.

On the other hand a short application of cold produces a shrinking in the caliber of the vessels of the skin in an afflicted area, a strong nervous stimulus, and a dilatation of the vessels of other parts of a body. Such short application of cold stimulates heart and respiration, quickening circulation, promoting improved interchange of gases in the lungs. This is followed by a local reaction in which the contracted skin vessels dilate again and a sensation of local warmth is produced. Longer applications of cold depress these functions and lower the body termperature. Injuries such as bruises and sprains, accompanied as they always are by local congestion and heat, are much benefited by a short local application of cold. Applied immediately after the injury it prevents excessive effusion of lymph and consequent swelling of the injured part. In disease there is a wide scope for this method of treatment in conditions such as excessive fever, meningitis, heat stroke, and so forth.

Alternative devices for general or local therapeutic heating or cooling of an animal or human body have been devised. U.S. Pat. No. 2,547,886 discloses a therapeutical device with a permanently sealed bag or pack containing an ambient temperature liquid permanently sealed in capsules. In a second embodiment of the device permanently sealed independent compartments contain an ambient temperature liquid permanently sealed in capsules.

U.S. Pat. No. 2,562,121 discloses a therapeutical device with a plurality of permanently sealed liquid-containing compartments having superimposed thereon air-containing compartments which cushion and insulate the liquid-containing compartments. The device is in the form of a strap for application to the human body.

U.S. Pat. No. 2,602,302 discloses a combination ice and hot pack with a plurality of independent and sealed fluid containing compartments. Each compartment is spaced from every other compartment by means of a flexible web of material which allows the device to be folded upon itself.

U.S. Pat. No. 2,697,424 discloses a therapeutic cold pack having front and back elastomeric sealed walls. The front wall has a small opening through which a slurry of ten percent isopropyl alcohol/water mixture is introduced. After the cold pack is filled with alcohol/-water mixture, the opening is closed by means of a rubber patch.

U.S Pat. No. 2,715,315 discloses a localized applicator for cooling body temperatures having a container within which a coolant such as carbon dioxide is positioned. Straps secure the applicator to the local body areas to be cooled.

U.S. Pat. No. 4,462,224 discloses an instant hot or cold, reusable cold pack having three compartments with one compartment containing a predetermined amount of solvent (water), a second compartment containing a predetermined amount of an exothermic solute (calcium chloride) or an endothermic solute (ammonium nitrate), and a third compartment containing a gelling agent (hydroxypropyl methylcellulose and propylene glycol) capable of reacting with the solvent-solute solution to produce a gel. The compartments are separated from one another by rupturable seams. Upon rupture of the solvent-solute seam, the solvent mixes with the solute to liberate or absorb heat to produce the desired heating or cooling effect. Once the solution has returned to ambient temperature, upon rupture of the gelling agent/solvent-solute seam, the gelling agent mixes with the solvent-solute solution to produce a reusable gel pack.

U.S. Pat. No. 4,575,097 discloses a therapeutic device and method for forming and using same, such therapeutic device having a plurality of chambers spaced from each other with adjacent chambers being serially connected by passageways. The chambers and passageways are filled with a thermal responsive material (water). The device is heated to a desired temperature prior to applying heat treatment to a body portion.

U.S. Pat. No. 4,592,358 discloses a therapeutic device having a plurality of compartments which can enclose a heat absorbing material, or a heat releasing material, or a high density material. The device can be firmly positioned on various body portions using one or more straps.

While the medical art use of various therapeutic devices for general and local heating and cooling of an animal or human body to dull pain, to alleviate disease, to reduce body temperature, and to improve circulation and respiration is well known, the above-described devices are limited in their convenience, versatility, economy, or effectiveness in applying either heat or cold to the affected area of the body. The principal limitations of such devices are their inherent inability to be compressibly and conformably disposed to body portions with minimal discomfort.

The device of the present invention not only can provide the requisite amount of compression but also can therapeutically treat large or small body portions while conforming to a variety of body contours. Moreover, the entire device or a component of the device may be repeatedly subjected to predetermined temperature conditions and reused indefinitely. As will be shown, the unique combination of features embodied in the present invention is an advance in the therapeutical treatment of animal and human diseases and injuries.

SUMMARY OF THE INVENTION

The reusable therapeutic device of the present invention may be used to treat physical injury to an animal or human body. It is particularly suited to treat physical injury to a large animal (such as a race horse, polo pony, show horse, and the like used in sporting events) by reducing inflammation, swelling, and excess heat produced by overexertion caused by strenuous activity. If such large animals are to achieve peak performance, their legs must be maintained in the best possible condition.

If an animal competes in more than one event per day, the therapeutic device can be applied when the animal is not competing. If the therapeutic device is not in use, it may be stored in an insulated container during such non-use periods. The therapeutic device may be applied to a body portion of an animal following strenuous activity or it may be worn by the animal to protect its legs, for example, while it is being transported from place to place. Leg protection is achieved because the pressure resulting from the animal kicking itself, bumping into the side of the transporting vehicle, and the like, is absorbed by resilient material of the therapeutic device.

In accordance with the teachings of the present invention a flexible, nonelastic, liquid impervious outer sheet has affixed to one of its broadsides a fabric backing material. Preferably, straps, belts, wrapping, or the like are affixed to the outer sheet to hold the position of the therapeutic device on a portion of an animal or human body or, alternatively, adhesive tape may be used to secure the position of the therapeutic device. Affixed to the other broadside of the fabric backing material is a layer of resilient material. A quilt-like array of separate packets containing a thermoresponsive mixture with each packet enclosed within a separate compartment is formed from a flexible, nonelastic, liquid impervious sheet. A broadside of the compartment sheet is releasably affixed to the other broadside of the layer of resilient material.

Prior to use the therapeutic device is subjected to a temperature environment to produce a predetermined temperature of the thermoresponsive material. The therapeutic device is particularly effective when extreme cold is required, because the extreme cold condition can penetrate through relatively thick layers of covering material (casts, bandages, and the like). When applied over such materials, swelling and pain are reduced until further medical attention, if required, can be obtained. On the other hand the therapeutic device can be directly applied to the skin of the afflicted area without damage. The therapeutic device can be conveniently transported in its elevated or depressed temperature state in an ordinary thermal chest to be available for use after an animal has competed in a sporting event, properly cooling down the animal after strenuous activity.

Because of its unique design, very little condensation forms leaving little or no mess. The therapeutic device can be manufactured in various sizes and shapes with straps, belts, bandages, or the like to conform to any body area requiring treatment. It is durable, reusable, economical, and practical. For example, if one or more of the packets containing the thermoresponsive mixture are damaged, the therapeutic device is still effective and any damaged packet can later be repaired or replaced. Although the therapeutic device is particularly effective for large animal use, it can with equal effectiveness be also used on humans.

The flexibility of the therapeutic device allows it to be applied to an animal anywhere and at anytime. Furthermore, because the behavior of animals is different than human behavior, the therapeutic device may be used on an animal without confining it or punishing it by strict action. In other words the natural movements and functions of the animal do not need to be restricted when using the therapeutic device. Most normal functions may be performed while an animal is undergoing treatment.

The therapeutic device is lightweight and causes minimal interruption of animal activity. Treatment is administered in such a manner so as to conform to similar situations that the animal has already adapted to, which means the device is easy for an animal to adapt to.

When using the device in its cold thermal state, the temperature of the therapeutic device would be the freezing temperature of the thermoresponsive material contained in the quilt-like packets and would eventually increase as the heat generated by an animal was absorbed, the frozen material of the therapeutic device, depending upon the amount of time used, amount of heat absorbed by the therapeutic device, heat capacity of the thermoresponsive material, and so forth.

These and other advantages and attainments of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

For a further understanding of the nature and object of the invention, reference should be had to the detailed description of the exemplary embodiment taken in connection with the appended drawings in which:

FIG. 1 is a perspective view of an animal body with portions thereof enwrapped with the reusable therapeutic device of this invention.

FIG. 2 is an perspective view of a fragmentarily shown human body with a forearm thereof enwrapped with the reusable therapeutic device of this invention.

FIG. 3 is a perspective view of the reusable therapeutic device of this invention.

FIG. 4 is an exploded perspective view of the reusable therapeutic device of this invention.

FIG. 5 is a fragmentary elevational view of the reusable therapeutic device of this invention as seen along line 5—5 of FIG. 3.

FIG. 6 is an enlarged elevational view of two members of an array of chambers each enclosing a packet containing a thermoresponsive mixture of the reusable therapeutic device of this invention as seen along 6—6 of FIG. 4.

DETAILED DESCRIPTION OF THE INVENTION

In the following description, like reference characters designate like or corresponding parts throughout the several views of the drawings. Also in the following description, it is to be understood that such terms as "forward", "rearward", "left", "right", "upwardly", "downwardly", and the like, are words of convenience and are not to be construed as limiting terms.

Referring now to the drawings, and particularly to FIGS. 3–4, there is illustrated a reusable therapeutic device, generally designated by the numeral 10 and constituting the preferred embodiment of the present invention, being shown assembled in FIG. 3 and partially disassembled in FIG. 4. In its preferred embodiment, device 10 combines a protective and insulative component with a heating and cooling component.

The heating and cooling component of device 10 is generally composed of a broadside of a first sheet of a flexible, nonelastic, liquid impervious material 12 juxtaposed to a broadside of a second sheet of a flexible, nonelastic, liquid impervious material 14, with sheets 12, 14 being selected from a group of materials consisting of polyvinyl chloride, polyethylene, polypropylene, polyethylene terephthalate, polyurethane, polyvinylidene chloride/polyvinyl chloride copolymer, and the like, but preferably polyvinyl chloride. Sheet 12 is securely engaged to sheet 14 so that an array of integral, noncommunicating chambers 16 is formed, such chambers 16 being spaced from each other.

Any one of several available methods such as heat sealing, stitching, and the like may be utilized to securely engage sheet 12 to sheet 14. For example, two polyester sheets, each of which are coated on one broadside with heat-sealing polyethylene, are arranged so that the heat-sealable polyethylene coatings will be in contact with each other to provide the desired seal. And preferably, two juxtaposed sheets 12, 14 are stitched together in a horizontally straight line of stitches starting in proximity of one of their edges and then parallelly stitched together in horizontal rows of stitches 18a–18g to provide to a plurality of slots of predetermined size. The stitching is repeated but in a direction perpendicular to the horizontal rows of stitches to form a plurality of noncommunicating chambers 16.

However, before the plurality of noncommunicating chambers 16 are formed and after a vertical row of stitches 20 is stitched in proximity of a second edge of sheets 12, 14 that is perpendicular to the first edge of sheets 12, 14, packets 22 are inserted in the slots formed by the rows of parallel horizontal stitches 18, 18a–18g so that there is one packet 22 per slot. After one packet 22 is inserted into each of the slots, a vertical line of stitches 20a is sewn to form and to enclose packets 22 snugly and individually in chambers 16. The process (inserting packets 22 into slots and sewing vertical lines of stitches 20, 20a–20e) is repeated until a quilt-like array of noncommunicating chambers 16 is formed each individually and snugly enclosing one packet 22.

Packets 22 are composed of a flexible, elastic, liquid impervious material and contain a mixture 24 of a thermoresponsive material and an antibacterial agent. Preferably, the thermoresponsive material is water and the antibacterial agent is chlorine. Such packets 22 (trademarked CUBIES) are commercially available in the United States from Reliable Industries, Inc., Gladstone, N.J.

In proximity of an end of the securely engaged sheets 12, 14, one component 26 of a complimentary back-to-back fastening means is affixed to a broadside of such sheets 12, 14. The other component 28 of such fastening means is affixed to a sheet 34 of flexible, resilient material. Such fastening means are formed by a plurality of pressure sensitive hook and loop fasteners, one component 26 comprising a hook element, while the other component 28 comprising a loop element. However, it is immaterial to the invention as to whether the hook element 26 or the loop element 28 is affixed to the securely engaged sheets 12, 14 as long as the other complimentary element is positioned opposite to the first element. Preferably, such fasteners are woven nylon hook and loop fasteners, commercially known as VELCRO.

The protective and insulative component of device 10 is generally composed of an outer covering sheet 30 of flexible, nonelastic, liquid impervious material with sheet 30 being selected from a group of materials consisting of polyvinyl chloride, polyethylene, polypropylene, polyethylene terephthalate, polyurethane, polyvinylidene chloride/polyvinyl chloride copolymer, and the like, but preferably polyvinyl chloride. In proximity of an end of a broadside of outer covering sheet 30 is affixed a second VELCRO hook fastener 36, while in proximity of an opposite end of the broadside of outer covering sheet 30 is affixed a second VELCRO loop fastener 38. Accordingly, whenever second hook fastener 36 engages second loop fastener 38, the two ends of outer covering sheet 30 become securely fastened to one another.

Outer covering sheet 30 has affixed to its other broadside a backing sheet 32 of supple fabric material. Affixed to the other broadside of backing sheet 32, preferably by means of a solvent based adhesive, is a sheet 34 of flexible resilient material. Sheet 34 is selected from a group of materials consisting polyurethane, polyisoprene, polybutadiene, polybutadiene-styrene, polyethylene-propylene, polychlorophene-chlorobutadiene, and the like, but preferably polyurethane.

In proximity of an end of the broadside of sheet 34 that is reverse to the broadside affixed to backing sheet 32 loop fastener 28 is affixed so as to be opposite hook fastener 26 which is affixed to securely engaged sheets 12, 14. Accordingly, the protective and insulative component of device 10 is releasably fastened to the heating and cooling component of device 10. Therefore, both components need not to be subjected to predetermined temperature conditions or to be stored in a thermally insulated container when not in use, only the heating and cooling component of device 10.

As can be seen in FIG. 1 and FIG. 2, the reusable therapeutic device 10 of the present invention can be conformably wrapped about various portions of an animal or human body. Additionally, reusable device 10 can be used for hot or cold temperature applications for various portions of an animal or human body conforming to the contours of such body portions even when the thermoresponsive mixture 24 is in a frozen state.

It is thought that the present invention and many of its attendant advantages will be understood from the foregoing description and it will be apparent that various changes may be made in the form, construction, and arrangement of the parts thereof without departing from the spirit and scope of the invention or sacrificing all of its material advantages, the form hereinabove described being merely a preferred or exemplary embodiment thereof.

I claim as my invention:

1. A reusable therapeutic device comprising:
   an array of noncommunicating chambers spaced from each other and formed by means of a broadside of a first flexible, nonelastic, liquid impervious sheet securely engaged to a broadside of a second flexible, nonelastic, liquid impervious sheet, having affixed in proximity of an end of a broadside of said securely engaged sheets a component of a complimentary back-to-back releasable fastening means;
   a plurality of flexible, elastic, liquid impervious packets containing a thermoresponsive mixture with one of the packets individually and snugly enclosed within one of the chambers;
   a sheet of flexible, resilient material having affixed in proximity of an end of a broadside thereof, the other component of the complimentary back-toback releasable fastening means, said other component being positioned opposite to the component affixed to said securely engaged sheets;

a backing sheet of supple fabric material with one broadside thereof affixed to the other broadside of the sheet of flexible, resilient material, and an outer covering sheet of flexible, nonelastic, liquid impervious material with one broadside thereof affixed to the other broadside of said backing sheet, said covering sheet having affixed in proximity of an end of a broadside thereof a component of a complimentary back-to-back releasable fastening means while having affixed in proximity of an opposite end of the broadside thereof the other component of said fastening means.

2. The reusable therapeutic device according to claim 1, wherein said chambers are permanently closed on all sides.

3. The reusable therapeutic device according to claim 1, wherein said flexible, nonelastic, liquid impervious material is selected from a group consisting of polyvinyl chloride, polyethylene, polypropylene, polyethylene terephthalate, polyurethane, polyvinylidene chloride/polyvinyl chloride copolymer, and the like, but preferably polyvinyl chloride.

4. The reusable therapeutic device according to claim 1, wherein said components of the complimentary back-to-back releasable fastening means are woven nylon hook and loop fasteners, commercially known as VELCRO.

5. The reusable therapeutic device according to claim 1, wherein said packets are composed of a flexible, elastic, liquid impervious material.

6. The reusable therapeutic device according to claim 1, wherein said packets contain a thermoresponsive mixture.

7. The reusable therapeutic device according to claim 6, wherein said thermoresponsive mixture is chlorinated water.

8. The reusable therapeutic device according to claim 1, wherein said packets are commercially known as CUBIES.

9. The reusable therapeutic device according to claim 1, wherein said flexible, resilient material is selected from a group consisting of polyurethane, polyisoprene, polybutadiene-styrene, polyethylene-propylene, polychlorophene-chlorabutadiene, and the like, but preferably polyurethane.

10. The reusable therapeutic device according to claim 1, wherein said device is adapted to be conformable to a portion of an animal or human body.

11. An applicator for therapeutical treatment of portions of an animal or human body combining protective and insulative means with heating and cooling means comprising:

an array of noncommunicating chambers spaced from each other and formed by means of a broadside of a first flexible, nonelastic, liquid impervious sheet securely engaged to a broadside of a second flexible, nonelastic, liquid impervious sheet, having affixed in proximity of an end of a broadside of said securely engaged sheets a component of a complimentary back-to-back releasable fastening means;

a plurality of flexible, elastic, liquid impervious packets containing a thermoresponsive mixture with one of the packets individually and snugly enclosed within one of the chambers;

a sheet of flexible, resilient material juxtaposed to one broadside of said securely engaged sheets;

a backing sheet of supple fabric material with one broadside thereof affixed to the other broadside of the sheet of flexible, resilient material; and an outer covering sheet of flexible, nonelastic, liquid impervious material with one broadside thereof affixed to the other broadside of said backing sheet, said covering sheet having affixed in proximity of an end of a broadside thereof a component of a complimentary back-to-back releasable fastening means while having affixed in proximity of an opposite end of the broadside thereof the other component of said fastening means.

12. The applicator according to claim 11, wherein said array of noncommunicating chambers with packets containing a thermoresponsive mixture enclosed therein is secured to a portion of an animal or human body with an elongated cloth wrapping.

13. The applicator according to claim 11, wherein the means for securing the applicator to a portion of an animal or human body is an elongated cloth wrapping.

14. The applicator according to claim 11, wherein said applicator is adapted to be conformable to a portion of an animal or human body.

15. A method for therapeutically heating or cooling portions of an animal or human body comprising:

providing an array of noncommunicating chambers spaced from each other and formed by means of a broadside of a first flexible, nonelastic, liquid impervious sheet securely engaged to a broadside of a second flexible, nonelastic, liquid impervious sheet, having affixed in proximity of an end of a broadside of said securely engaged sheets a component of a complimentary back-to-back releasable fastening means;

enclosing a plurality of flexible, elastic, liquid impervious packets containing a thermoresponsive mixture with one of the packets individually and snugly enclosed within one of the chambers;

affixing to a sheet of flexible, resilient material in proximity of an end of a broadside thereof, the other component of the complimentary back-to-back releasable fastening means, said other component being positioned opposite to the component affixed to said securely engaged sheets;

securing a backing sheet of supple fabric material with one broadside thereof affixed to the other broadside of the sheet of flexible, resilient material;

providing an outer covering sheet of flexible, nonelastic, liquid impervious material with one broadside thereof affixed to the other broadside of said backing sheet, said covering sheet having affixed in proximity of an end of a broadside thereof a component of a complimentary back-to-back releasable fastening means while having affixed in proximity of an opposite end of the broadside thereof the other component of said fastening means;

subjecting the array of noncommunicating spaced chambers with said packets containing a thermoresponsive mixture enclosed therein to a predetermined temperature environment; and juxtaposing the array of noncommunicating spaced chambers with said packets containing a thermoresponsive mixture having a predetermined temperature with the portion of an animal or human body to be treated.

16. The method for therapeutically heating or cooling portions of an animal or human body according to claim 15, wherein stitching means are used to provide for said array of noncommunicating chambers.

17. The method for therapeutically heating or cooling portions of an animal or human body according to claim 15, wherein heat sealing means are used to provide for said array of noncommunicating chambers.

18. The method for therapeutically heating or cooling portions of an animal or human body according to claim 15, wherein a thermally insulated container is used to store the array of noncommunicating chambers with packets containing a thermoresponsive mixture that has been subjected to a predetermined temperature.

19. The method for therapeutically heating or cooling portions of an animal or human body according to claim 15, wherein said backing sheet of supple fabric material is affixed to the other broadside of said sheet of flexible, resilient material with a solvent based adhesive.

20. The method for therapeutically heating or cooling portions of an animal or human body according to claim 15, wherein said treatment means can be adapted to be conformable to the contours of various portions of an animal or human body.

* * * * *